(12) United States Patent
Sathe et al.

(10) Patent No.: US 11,020,390 B2
(45) Date of Patent: Jun. 1, 2021

(54) BIOEQUIVALENT PHARMACEUTICAL COMPOSITION OF VORTIOXETINE HYDROBROMIDE

(71) Applicant: UNICHEM LABORATORIES LTD, Mumbai (IN)

(72) Inventors: Dhananjay Sathe, Maharashtra (IN); Bijay Kumar Padhi, Telengana (IN); Pravin Kumar Maurya, Maharashtra (IN)

(73) Assignee: UNICHEM LABORATORIES LTD, Mumbai (IN)

( * ) Notice: Subject to any disclaimer, the term of this patent is extended or adjusted under 35 U.S.C. 154(b) by 96 days.

(21) Appl. No.: 16/485,869

(22) PCT Filed: Feb. 15, 2018

(86) PCT No.: PCT/IB2018/050918
§ 371 (c)(1),
(2) Date: Aug. 14, 2019

(87) PCT Pub. No.: WO2018/150344
PCT Pub. Date: Aug. 23, 2018

(65) Prior Publication Data
US 2020/0188391 A1 Jun. 18, 2020

(30) Foreign Application Priority Data

Feb. 17, 2017 (IN) .............................. 201721005626
Feb. 14, 2018 (IN) .............................. 201821005562

(51) Int. Cl.
*A61K 31/496* (2006.01)
*A61K 9/20* (2006.01)

(52) U.S. Cl.
CPC .......... *A61K 31/496* (2013.01); *A61K 9/2013* (2013.01); *A61K 9/2054* (2013.01); *A61K 9/2059* (2013.01)

(58) Field of Classification Search
CPC .. A61K 31/496; A61K 9/2013; A61K 9/2054; A61K 9/2059
See application file for complete search history.

(56) References Cited

U.S. PATENT DOCUMENTS 9,101,626 B2 * 8/2015 Faldt ...................... A61P 11/00
2016/0214949 A1 * 7/2016 Dwivedi ............ C07D 295/096

* cited by examiner

*Primary Examiner* — Zohreh A Fay
(74) *Attorney, Agent, or Firm* — Campbell Stephenson LLP (57) ABSTRACT

The invention relates to vortioxetine hydrobromide having particle size distribution of D98 100-200μ, D50 35-90μ and D5 7-30μ as well as to a stable, reproducible and bioequivalent pharmaceutical composition comprising vortioxetine hydrobromide having particle size distribution of D98 100-200μ, D50 35-90μ and D5 7-30μ and one or more pharmaceutically acceptable excipient. It is produced by wet granulation techniques.

10 Claims, 7 Drawing Sheets

Process flow chart for manufacturing of vortioxetinehydrobromide tablets 5 mg, 10 mg, and 20 mg

Comparative dissolution profile of Trintellix® (Vortioxetine) tablets 5mg and vortioxetine tablets 5mg (Test)

FIGURE 2

Figure 3: Comparative dissolution profile of Trintellix®(Vortioxetine) tablets 10mg and vortioxetine tablets 10mg (Test)

Comparative dissolution profile of Trintellix®(Vortioxetine) tablets 20mg and Vortioxetine tablets 20mg (Test)

FIGURE 5

Accelerated stability data of vortioxetinehydrobromide tablets 5 mg

| Sr. | Parameters | | Limits | Initial | 40°C/ 75%RH | | |
|---|---|---|---|---|---|---|---|
| | | | | | 1 Month | 3 Months | 6 Months |
| 1 | Description | | Pink colour, almond shaped biconvex film coated tablet, debossed with "335" on one side and "U" on the other side | Pink colour, almond shaped biconvex film coated tablet, debossed with "335" on one side and "U" on the other side | Pink colour, almond shaped biconvex film coated tablet, debossed with "335" on one side and "U" on the other side | Pink colour, almond shaped biconvex film coated tablet, debossed with "335" on one side and "U" on the other side | Pink colour, almond shaped biconvex film coated tablet, debossed with "335" on one side and "U" on the other side |
| 2 | Dissolution | 10 min | NLT 80% (Q) of the labeled amount dissolved in 30 minutes | 97% | 92% | 93% | 89% |
| | | 15min | | 98% | 96% | 99% | 95% |
| | | 30min | | 97% | 96% | 99% | 95% |
| | | 45 min | | 97% | 97% | 99% | 97% |
| 3 | Organic impurities (%w/w) | | | | | | |
| a. | Any other individual unidentified impurity | | NMT 0.2% | BRT | 0.05% | 0.11%,0.05%, 0.05% | 0.2%,0.05%, 0.09%,0.07% |
| b. | Total impurities≥ 0.05 % | | NMT 1% | BRT | 0.05% | 0.21% | 0.41% |
| 4 | Assay | | 90 to 110% | 100.1% | 100.3% | 100.3% | 97.8% |

Note: BRT: Below reporting threshold
NLT: Not lee than
NMT: Not more than

Accelerated stability data of vortioxetinehydrobromide tablets 10 mg

| Sr. No. | Parameters | | Limits | Initial | 40°C/ 75 %RH | | |
|---|---|---|---|---|---|---|---|
| | | | | | 1 Month | 3 Months | 6 Months |
| 1 | Description | | Yellow colour, almond shaped biconvex film coated tablet, debossed with "336" on one side and "U" on the other side | Yellow colour, almond shaped biconvex film coated tablet, debossed with "336" on one side and "U" on the other side | Yellow colour, almond shaped biconvex film coated tablet, debossed with "336" on one side and "U" on the other side | Yellow colour, almond shaped biconvex film coated tablet, debossed with "336" on one side and "U" on the other side | Yellow colour, almond shaped biconvex film coated tablet, debossed with "336" on one side and "U" on the other side |
| 2 | % Dissolution | 10 min | NLT 80% (Q) of the labeled amount dissolved in 30 minutes | 99% | 86% | 97% | 86% |
| | | 15min | | 101% | 97% | 102% | 98% |
| | | 30min | | 101% | 99% | 103% | 99% |
| | | 45min | | 101% | 99% | 103% | 100% |
| 3 | Related substances (%) | | | | | | |
| a. | Any other individual unidentified impurity | | NMT 0.20% | BRT | 0.06% | 0.06% | 0.13%,0.05%, 0.06% |
| b. | Total Impurities ≥ 0.05 % | | NMT 1.00% | BRT | 0.06% | 0.06% | 0.24% |
| 4 | Assay | | 90.0 to 110.0% | 101.1% | 101.8% | 102.5% | 99.3% |

Note: BRT: Below reporting threshold
NLT: Not less than
NMT: Not more than

FIGURE 6

Accelerated stability data of vortioxetinehydrobromide tablets 20 mg

| Sr. No. | Parameters | | Limits | Initial | 40°C/ 75 %RH | | |
|---|---|---|---|---|---|---|---|
| | | | | | 1 Month | 3 Months | 6 Months |
| 1 | Description | | Red colour, almond shaped biconvex film coated tablet, debossed with "338" on one side and "U" on the other side | Red colour, almond shaped biconvex film coated tablet, debossed with "338" on one side and "U" on the other side. | Red colour, almond shaped biconvex film coated tablet, debossed with "338" on one side and "U" on other side. | Red colour, almond shaped biconvex film coated tablet, debossed with "338" on one side and "U" on the other side. | Red colour, almond shaped biconvex film coated tablet, debossed with "338" on one side and "U" on the other side. |
| 2 | % Dissolution | 10min | NLT 80% (Q) of the labeled amount dissolved in 30 min | 97% | 93% | 89% | 97% |
| | | 15 min | | 100% | 96% | 94% | 101% |
| | | 30 min | | 101% | 97% | 95% | 101% |
| | | 45 min | | 100% | 97% | 95% | 102% |
| 3 | Related substances (%) | | | | | | |
| a. | Any other individual unidentified impurity | | NMT 0.20% | BRT | BRT | BRT | BRT |
| b. | Total Impurities ≥ 0.05 % | | NMT 1.00% | BRT | BRT | BRT | BRT |
| 4 | Assay | | 90.0 to110.0% | 98.5% | 98.7% | 98.3% | 98.0% |

Note: BRT: Below reporting threshold
NLT: Not less than
NMT: Not more than

FIGURE 7

BIOEQUIVALENT PHARMACEUTICAL COMPOSITION OF VORTIOXETINE HYDROBROMIDE

CROSS-REFERENCE TO RELATED APPLICATION

This application is a national stage application filed under 35 U.S.C. 371 of International Application No. PCT/IB2018/050918, filed Feb. 15, 2018, which is incorporated by reference herein in its entirety.

International Application No. PCT/IB2018/050918 claims the benefit of India Application No. 201721005626 filed Feb. 17, 2017 and India Application No. 201821005562 filed Feb. 14, 2018, which are incorporated by reference herein in its entirety.

FIELD OF THE INVENTION

The present invention relates to vortioxetine hydrobromide having particle size distribution of D98 100-200μ, D50 35-90μ and D5 7-30μ and a stable, reproducible and bioequivalent pharmaceutical composition comprising vortioxetine hydrobromide having PSD of D98 100-200μ, D50 35-90μ and D5 7-30μ and one or more pharmaceutically acceptable excipients. More particularly, the present invention relates to a bioequivalent pharmaceutical composition comprising vortioxetine hydrobromide and one or more pharmaceutically acceptable excipients wherein vortioxetine hydrobromide has particle size distribution of D98 100-200μ, D50 35-90μ and D5 7-30μ.

Vortioxetine hydrobromide 1-[2-(2,4-Dimethyl-phenylsulfanyl)-phenyl]-piperazine, hydrobromide is used in the treatment for major depressive disorder, is claimed generically as well as specifically in U.S. Pat. No. 7,144,884. Its equivalent U.S. Pat. No. 8,476,279 and IN227963 claimed pharmaceutical composition. Both these patents are silent on stability aspects of composition and how to prepare the composition. They are also silent on the aspects of polymorphic stability of vortioxetine hydrobromide either as compound or when present in the composition.

U.S. Pat. No. 8,722,684 claims vortioxetine hydrobromide characterized by certain XRPD peaks stated numerically as well as by referring to figures stated in the patent. It also claims the compound according to claim 2, which compound has a particle size distribution corresponding to D98%: 650-680 μm; D50%: 230-250 μm; and D5%: 40-60 μm; D98%: 370-390 μm; D50%: 100-120 μm; and D5%: 5-15 μm; D98%: 100-125 μm; D50%: 15-25 μm; and D5%: 1-3 μm; or D98: 50-70 μm; D50%: 3-7 μm; and D5%: 0.5-2 μm. It also claims compositions with specific contents of specified ingredients. It also claims compositions prepared by wet granulations. In the detailed description it specifically states that "The size of the crystals used for preparing tablets comprising compounds of the present invention are of significance. If the crystals are too small they may stick to the plunger in the tablet machines. On the other hand, they cannot be too large either. The dissolution rate in the intestines decrease when crystal size increases. Hence, if the crystals are too large it may compromise the bioavailability of the compounds. Particle size distribution may be described using quantiles, e.g. D5%, D10%, D50%, D90%, D95% and D98%. As used herein, "particle size distribution" means the cumulative volume size distribution of equivalent spherical diameters as determined by laser diffraction at 1 bar dispersive pressure in a Sympatec Helos equipment." It has not substantiated the said invention by vortioxetine of the said PSD ranges.

WO2014177491 describes pharmaceutical composition of amorphous vortioxetine hydrobromide and an adsorbent and the process to produce the same.

WO2015044394 describes the process to prepare pharmaceutical composition comprising 0.1 mg to 10 mg of vortioxetine hydrobromide wherein vortioxetine hydrobromide has PSD of D90 of less than 50μ.

WO2015044963 also published as US20160214949 describes amorphous vortioxetine hydrobromide, an amorphous solid dispersion of vortioxetine free base or salts, a process for the preparation of an amorphous solid dispersion of vortioxetine or salts thereof, an amorphous solid dispersion of vortioxetine hydrobromide substantially free from crystalline forms and residual solvents. In claim 22 and in claim 23 it claims an amorphous vortioxetine hydrobromide having particle size distributions, D(10) of about 50 μm or less, D(50) of about 200 μm or less, and D(90) of about 400 μm or less; or D(10) of about 25 μm or less, D(50) of about 100 μm or less, D(90) of about 250 μm or less and a pharmaceutical composition comprising an amorphous vortioxetine hydrobromide having a particle size distributions, D(10) of about 50 μm or less, D(50) of about 200 μm or less, D(90) of about 400 μm or less; or D(10) of about 25 μm or less, D(50) of about 100 μm or less, D(90) of about 250 μm or less together with one or more of pharmaceutically acceptable carriers, excipients or diluents.

WO2016062860 in claim 1 claims a pharmaceutical composition comprising a solid solution or solid dispersion of amorphous vortioxetine hydrobromide in at least one organic carrier, and at least one further ingredient being contained in an amount of about 0.01 to about 80% by weight relative to the weight of the solid solution or solid dispersion.

The solubility of vortioxetine hydrobromide salt in water is relatively poor. Increase in crystal size or particle jeopardizes the solubility. As has been described in the prior art, it is the particle size of the vortioxetine hydrobromide which is of critical importance to produce desirable composition. Unique behavior of vortioxetine hydrobromide, its vulnerability to undergo polymorphic change, and the critical nature of crystal and their size impose severe limitations on use of vortioxetine hydrobromide crystals which are of bigger size.

In view of the relatively poor solubility of vortioxetine, critical nature of crystal sizes or particle size, there is a need to provide bioequivalent pharmaceutical compositions containing vortioxetine hydrobromide that is different from the known particle sizes used in the prior art. Thus the new particle size distribution is of critical importance being novel and non-obvious. There is a need to prepare and provide stable, reproducible and bioequivalent pharmaceutical compositions containing vortioxetine hydrobromide of different particle size distribution.

It has now been unexpectedly found that pharmaceutical compositions containing vortioxetine hydrobromide of different particle size distribution also produce similar in-vitro and in-vivo profile as that of innovator composition.

It has been surprisingly found that even when PSD as prescribed by innovator in U.S. Pat. No. 8,722,684 is not followed, it is possible to produce a stable, reproducible and bioequivalent pharmaceutical compositions containing vortioxetine hydrobromide.

Another peculiarity of the prior art indicates that it is necessary to use wet granulation techniques when vortioxetine hydrobromide of the PSD as prescribed and taught in U.S. Pat. No. 8,722,684 is to be used. Wet granulation technique is of critical importance according to U.S. Pat. No. 8,722,684 for the PSD taught by U.S. Pat. No. 8,722,684. Surprisingly it is found that even when vortioxetine hydrobromide of different PSD is used, still it is possible to produce stable, reproducible and bioequivalent pharmaceutical compositions containing vortioxetine hydrobromide by wet granulation technique.

More particularly it was a surprise to notice that when vortioxetine hydrobromide having PSD of D98 100-200μ, D50 35-90μ and D5 7-30μ is used, the composition produced is stable, reproducible and bioequivalent.

OBJECT OF THE INVENTION

The main object of present invention is to provide vortioxetine hydrobromide having particle size distribution corresponding to D98 100-200μ, D50 35-90μ and D5 7-30μ.

Another object of the invention is to provide a stable, reproducible and bioequivalent pharmaceutical composition comprising vortioxetine hydrobromide and one or more pharmaceutically acceptable excipient.

Another object of the invention is to provide a stable, reproducible and bioequivalent pharmaceutical composition comprising vortioxetine hydrobromide having PSD of D98 100-200μ, D50 35-90μ and D5 7-30μ and one or more pharmaceutically acceptable excipient.

Yet another object of present invention is to provide a stable, reproducible and bioequivalent pharmaceutical composition comprising vortioxetine hydrobromide having PSD of D98 100-200μ, D50 35-90μ and D5 7-30μ and one or more pharmaceutically acceptable excipient and which is produced by spray granulation, wet granulation.

SUMMARY OF THE INVENTION

The present invention relates to vortioxetine hydrobromide having particle size distribution corresponding to D98 100-200μ, D50 35-90μ and D5 7-30μ.

The present invention relates to a stable, reproducible and bioequivalent pharmaceutical composition comprising vortioxetine hydrobromide and one or more pharmaceutically acceptable excipient.

The present invention particularly relates to a stable, reproducible and bioequivalent pharmaceutical composition comprising vortioxetine hydrobromide having PSD of D98 100-200μ, D50 35-90μ and D5 7-30μ and one or more pharmaceutically acceptable excipient.

Also the present invention particularly relates to a stable, reproducible and bioequivalent pharmaceutical composition comprising vortioxetine hydrobromide having PSD of D98 100-200μ, D50 35-90μ and D5 7-30μ and one or more pharmaceutically acceptable excipient and which is produced by spray granulation, wet granulation.

DETAILED DESCRIPTION OF THE INVENTION

According to main object of the invention, there is provided vortioxetine hydrobromide having Particle Size distribution corresponding to D98 100-200μ, D50 35-90μ and D5 7-30μ.

According to another object of the invention there is provided a stable, reproducible and bioequivalent pharmaceutical composition comprising vortioxetine hydrobromide and one or more pharmaceutically acceptable excipient.

According to another object of the invention there is provided a stable, reproducible and bioequivalent pharmaceutical composition comprising vortioxetine hydrobromide having PSD of D98 100-200μ, D50 35-90μ and D5 7-30μ and one or more pharmaceutically acceptable excipient.

According to yet another object, there is provided a stable, reproducible and bioequivalent pharmaceutical composition comprising vortioxetine hydrobromide having PSD of D98 100-200μ, D50 35-90μ and D5 7-30μ and one or more pharmaceutically acceptable excipient and which is produced by spray granulation, wet granulation.

Terms "Vortioxetine Tablet(s)" and "Vortioxetine Hydrobromide Tablet(s)" are used interchangeably and mean tablet(s) comprising vortioxetine hydrobromide as an active ingredient.

The term "composition" as used herein refers to equivalents thereof, including but not limited to cores, coated cores, pellets, micro-pellets, pills, compressed tablets, granules, spheres, capsules and the like.

The term "pharmaceutically acceptable" as used herein means that which is useful in preparing a pharmaceutical composition that is generally safe and non-toxic and compatible with vortioxetine hydrobromide under test conditions.

The term "tablet" is intended to encompass compressed pharmaceutical dosage forms of all shape and size, whether coated or uncoated.

The term "stable and reproducible" as used herein means that the composition is stable when stored at stability conditions as per ICH stability guidelines and that the process described produces a stable and bioequivalent formulation repeatedly.

The term "bioequivalent" as used herein means that a formulation that has the same pharmacologic potency and bioavailability as that of reference formulation containing same active agent at the same dose. Two products or formulations containing the same active ingredient are bioequivalent if their rates and extents of absorption i.e., bioavailability are the same.

The term 'similarity factor' or 'f2 factor' as used herein refers to one way of comparing dissolution profiles of two different products. This model-independent mathematical approach compares the dissolution profile of the two products: test and reference or two strengths. Tests are recommended to be performed under the same test conditions. The dissolution time points for both the profiles should be the same. An f2 value of 50 or greater (50-100) ensures sameness or equivalence of two curves, and thus equivalent performance of the two products, in-vitro.

The term PSD as used herein means 'Particle Size Distribution'. The term RH as used herein means 'Relative Humidity'. The term ASTM as used herein means 'American Society for Testing and Materials'. The term a as used herein means 'micron'. The term RPM as used herein means 'Revolutions per Minutes'. The term LOD as used herein means 'Loss on Drying.' The term "AUC" as used herein means area under the plasma drug concentration-time curve reflects the actual body exposure to drug after administration of a dose of the drug. The term "Cmax" as used herein means the maximum (or peak) serum concentration that a drug achieves in a specified compartment or test area of the body after the drug has been administrated and before the administration of a second dose. Vortioxetine hydrobromide is milled and or micronized to produce the vortioxetine hydrobromide having Particle Size distribution corresponding to D98 100-200μ, D50 35-90μ and D5 7-30μ. Particle size distribution is described herein, using quantiles, e.g. D5%, D50% and D98%. As used herein, "particle size distribution" means the cumulative volume size distribution of equivalent spherical diameters as determined by laser diffraction in Malvern Mastersizer 2000 equipment in wet method with liquid Paraffin.

Novelty of the vortioxetine hydrobromide of the PSD D98 100-200μ, D50 35-90μ and D5 7-30μ presides in the fact that it was not reported in the prior art that vortioxetine hydrobromide of D98 100-200μ, D50 35-90μ and D5 7-30μ PSD produces bioequivalent pharmaceutical composition. Non-obviousness of the invention resides in the fact that in the light of prior art teachings, nobody would ever imagine that vortioxetine hydrobromide of D98 100-200μ, D50 35-90μ and D5 7-30μ PSD would ever produce bioequivalent pharmaceutical composition.

Prior art does teach wet granulation of vortioxetine hydrobromide. But it severely and categorically limits the use of wet granulation of vortioxetine hydrobromide of the PSD as prescribed in U.S. Pat. No. 8,722,684.

Novelty and non-obviousness of the invention resides in the fact that prior art teachings neither teach nor do they ever support imagination that the process of wet granulation of vortioxetine hydrobromide of D98 100-200μ, D50 35-90μ and D5 7-30μ PSD would produce bioequivalent pharmaceutical composition.

WO2015044963 also published as US20160214949 deals with amorphous vortioxetine hydrobromide and does not anticipate present invention or does not render present invention obvious.

The pharmaceutical composition of the present invention comprise one or more pharmaceutically acceptable excipients which include, but are not limited to binders, diluents, disintegrants, lubricants, glidants, coating agents, plasticizers, coloring agent, viscosity enhancers, and the like and the combinations thereof.

Pharmaceutical ingredients such as corn starch, potato starch, talcum, magnesium stearate, gelatin, lactose, gums, and the like and other adjuvants or additives such as colouring agents, flavouring agents, preservatives etc. may be used provided that they are compatible with vortioxetine hydrobromide under test conditions.

Diluents include, but are not limited to microcrystalline cellulose (MCC), micro fine cellulose, powdered cellulose, lactose, dibasic calcium phosphate, tribasic calcium phosphate, starch, pre-gelatinized starch, calcium carbonate, calcium sulfate, magnesium carbonate, magnesium oxide, dextrates, dextrin, dextrose, kaolin, maltodextrin, mannitol, sucrose, methyl dextrin, sorbitol, the like and the combinations thereof.

Binders include but are not limited to, polyvinylpyrrolidone (povidone, PVP), polyethylene glycol (PEG), cross-linked polyvinylpyrrolidone, cellulose derivatives (such as hydroxymethyl cellulose, hydroxypropyl cellulose (HPC), carboxymethylcellulose sodium, ethyl cellulose, hydroxylethylcellose, hydroxypropyl methylcellulose), sucrose, alginic acid or sodium alginate, carbomer, cottonseed oil, dextrin, dextrose, guar gum, hydrogenated vegetable oil type I, magnesium aluminium silicate, maltodextrin, maltose, polydextrose, polyethylene oxide, stearic acid and zein and the combinations thereof.

Disintegrants include, but are not limited to carboxymethylcellulose calcium, carboxymethylcellulose sodium, croscarmellose sodium, crospovidone, polacrilin potassium, sodium alginate and sodium starch glycolate (SSG) and the combinations thereof.

Lubricants according to the present invention include but are not limited to magnesium stearate, aluminium stearate, sucrose stearate, stearic acid, talc, fumaric acid, palmitic acid, sodium stearyl fumarate, glyceryl monostearate, carnauba wax, hydrogenated vegetable oils, mineral oil, polyethylene glycols and the like and the combinations thereof.

In one embodiment there is provided vortioxetine hydrobromide having Particle Size distribution corresponding to D98 100-200μ, D50 35-90μ and D5 7-30μ. Vortioxetine hydrobromide produced in bulk drug plant is milled and optionally micronized to produce vortioxetine hydrobromide having particle size distribution corresponding to D98 100-200μ, D50 35-90μ and D5 7-30μ. Conventionally used milling equipment is used to produce vortioxetine hydrobromide of this PSD.

In one embodiment the present invention provides a stable, reproducible and bioequivalent pharmaceutical composition comprising vortioxetine hydrobromide.

In an embodiment the present invention provides a stable, reproducible and bioequivalent pharmaceutical composition comprising vortioxetine hydrobromide having PSD of D98 100-200μ, D50 35-90μ and D5 7-30μ.

In an embodiment the present invention provides a stable, reproducible and bioequivalent pharmaceutical composition comprising vortioxetine hydrobromide having PSD of D98 100-200μ, D50 35-90μ and D5 7-30μ which is produced by wet granulation.

After selecting relative % of the ingredients as per regulatory guidelines for lower strengths, lower strengths which are similar to 20 mg strength are developed.

The pharmaceutical composition comprising vortioxetine hydrobromide having PSD of D98 100-200μ, D50 35-90μ and D5 7-30μ provides a stable and reproducible formulation which shows similarity factor value of more than 50 when dissolution of the formulation is compared with innovators product Trintellix 20 mg.

The pharmaceutical composition comprising vortioxetine hydrobromide having PSD of D98 100-200μ, D50 35-90μ and D5 7-30μ provides a stable and reproducible formulation which shows similarity factor value of more than 50 when dissolution of the formulation is compared with innovators product Trintellix 10 mg.

The pharmaceutical composition comprising vortioxetine hydrobromide having PSD of D98 100-200μ, D50 35-90μ and D5 7-30μ provides a stable and reproducible formulation which shows similarity factor value of more than 50 when dissolution of the formulation is compared with innovators product Trintellix 5 mg.

When in-vivo testing and comparison is done, the composition of the present invention shows similarity factor of more than 50 when compared with innovator product Trintellix 20 mg. Cmax, AUC are depicted in the tables titled "Bioequivalence Summary Table of Cmax" and "Bioequivalence Summary Table of AUC0-72".

The pharmaceutical composition of the invention may be present in the form of a tablet, capsule, powder, disc, caplet, granules, pellets, tablet in tablet, tablet in capsule, pellets in capsule, powder in capsule, granules in capsule and other dosage forms suitable for oral administration. The tablets may further be coated with film forming polymers.

The process to prepare pharmaceutical composition by wet granulation is provided. The process comprises the steps of sifting and mixing of diluent/s binder and disintegrant followed by granulating them with water and drying the granules, followed by sizing of dried granules and blending them diluent and disintegrant, followed by lubrication and compression.

In a preferred embodiment the pharmaceutical composition of the present invention is prepared by wet granulation process, wherein the process comprised the steps of:
 a. Dispensing all the ingredients as per formula and maintaining the environmental conditions of the temperature and RH less than 25° C. and RH 50% respectively.
 b. Co-sifting vortioxetine hydrobromide of the PSD D98 100-200μ, D50 35-90μ and D5 7-30μ with mannitol, hydroxypropyl cellulose through mesh no.: #40 ASTM twice.
 c. Sifting microcrystalline cellulose and sodium starch glycolate through mesh no.: #40 ASTM.
 d. Transferring Step (b) and (c) contents to Rapid Mixer Granulator (RMG) & dry mix for 20 min at an impeller speed of 100 RPM (Slow).
 e. Granulating the contents of step (d) in RMG with purified water using peristaltic pump.
 f. Drying the granules of step (e) in Fluid Bed Dryer (FBD) at 55° C. to obtain LOD NMT 4.0%.
 g. Sifting the dried granules of step (f) through mesh #30 ASTM using vibro sifter and collecting in a double-lined polyethylene bag.
 h. Milling the retentions of step (g) through co-mill/multi-mill fitted with 1/1.5 mm screen.
 i. Sifting the milled granules of step (g) through mesh #30 ASTM using vibro sifter, mixing with step (f) granules and transferring into the blender.
 j. Sifting mannitol and sodium starch glycolate through mesh #40 ASTM using vibro sifter and adding to step (i) blender containing granules and mix for 10 min at 16 rpm.
 k. Sift magnesium stearate through mesh #60 ASTM using vibro sifter and add to step (j) blender containing granules and mixing for 3 min at 16 rpm.
 l. Compressing the lubricated blend of step (k) with respective punches.
 m. Coating the compressed tablet with respective coating material as per unit formula table to achieve the approximate weight gain 3% w/w.

Alternatively the procedure to be followed is as follows:
 a. Sifting and mixing: Sifting vortioxetine hydrobromide of the PSD D98 100-200μ, D50 35-90μ and D5 7-30μ individually or with one or more of microcrystalline cellulose, mannitol, HPC, SSG through #40 sieve and mix in Rapid mix Granulator (RMG), to obtain pre-granulation blend.
 b. Granulation: Granulate the pre-granulation blend obtained in step (a) with purified water to obtain granules.
 c. Drying and Sizing: Dry the granules obtained in step (b), in fluid bed dryer to obtain the required LOD and size through #30 sieve to prepare sized granules.
 d. Blending: Blend the sized granules obtained in step (c), with mannitol and SSG at 16 RPM to obtain pre-lubrication blend.
 e. Lubrication: Lubricate with pre-lubrication blend prepared in step (d), with magnesium stearate at 16 RPM to obtain lubricated granules.
 f. Compression: Compress the lubricated granules obtained in step (e) into tablets by using 8.4×5.0 mm almond shape punch.
 g. Coating: Coat the compressed tablet prepared in Step (f), using Opadry suspension to achieve required weight gain.

The tablets may optionally be coated with a film coat, which provides different aesthetic appeal. Film coat also provides moisture protection, taste masking etc. Coating agents include, but not limited to polyvinyl alcohol, hydroxypropyl methylcellulose, carboxymethyl cellulose and like. Preferably coating is carried out using coating agents approved by Food Drugs and Administration (FDA) such as Opadry®.

EXAMPLES

The present invention is described in more detail by way of the following examples, but scope of the present invention is not limited thereto.

Vortioxetine hydrobromide is milled and optionally micronized to produce vortioxetine hydrobromide having particle size distribution corresponding to D98 100-200μ, D50 35-90μ and D5 7-30μ. This vortioxetine hydrobromide having particle size distribution corresponding to D98 100-200μ, D50 35-90μ and D5 7-30μ is used in subsequent examples to prepare the pharmaceutical composition.

Example 1: the Composition Comprising Vortioxetine Hydrobromide of the PSD D98 100-200μ, D50 35-90μ and D5 7-30μ

| | | | Quantity/Tablet (mg) | | |
|---|---|---|---|---|---|
| Sr. | Ingredients | Grade | 5 mg | 10 mg | 20 mg |
| A. | | Dry Mix | | | |
| 1 | Vortioxetine Hydrobromide | IH | 6.36 | 12.71 | 25.42 |
| 2 | Mannitol | USP | 25 | 50 | 50 |
| 3 | Microcrystalline Cellulose | USP/NF | 27.9 | 55.79 | 43.08 |
| 4 | Hydroxypropyl Cellulose | NF | 2.25 | 4.5 | 4.5 |
| 5 | Sodium Starch Glycolate | USP/NF | 1.25 | 2.5 | 2.5 |
| B. | | Granulating solution | | | |
| 6. | Purified Water | USP/Ph. Eur./BP/IP | q.s. | q.s. | q.s. |
| C. | | Extra granular | | | |
| 7. | Mannitol | USP | 10.75 | 21.5 | 21.5 |
| 8. | Sodium Starch Glycolate | USP/NF | 0.25 | 0.5 | 0.5 |
| 9. | Magnesium Stearate | USP/NF | 1.25 | 2.5 | 2.5 |
| | Core Tablet Weight | | 75 | 150 | 150 |
| D. | | Film Coating | | | |
| 10. | Opadry Pink | IH | 2.55 | — | — |
| | Opadry Yellow | | — | 4.5 | — |
| | Opadry Red | | — | — | 4.5 |

-continued

| Sr. | Ingredients | Grade | Quantity/Tablet (mg) | | |
| --- | --- | --- | --- | --- | --- |
| | | | 5 mg | 10 mg | 20 mg |
| 11. | Purified Water | USP/Ph. Eur./BP/IP | q.s. | q.s. | q.s. |
| | Coated Tablet Weight | | 77.25 | 154.5 | 154.5 |

Example 2: Process to Prepare the Tablet Composition a. Dispensed all the ingredients as per unit formula. Kept the temperature and RH less than 25° C. and RH 50% respectively.
b. Co-sifted API Vortioxetine Hydrobromide of the PSD D98 100-200µ, D50 35-90µ and D5 7-30µ with Mannitol, HPC through mesh no.: #40 ASTM twice.
c. Sifted MCC and SSG through mesh no.: #40 ASTM.
d. Transferred Step-2 and 3 contents to Rapid mixer granulator (RMG) and dry mix for 20 min at an impeller speed of 100 RPM (Slow).
e. Granulated the contents of step (d) in RMG with purified water using peristaltic pump.
f. Dried the granules of step (e) in Fluid Bed Dryer (FBD) at 55° C. to obtain LOD NMT 4%.
g. Sifted the dried granules of step (f) through mesh #30 ASTM using vibro sifter and collect in a double-lined polyethylene bag.
h. Milled the retentions of step (g) through co-mill/multi-mill 1/1.5 mm screen.
i. Sifted the milled granules of step (h) through mesh #30 ASTM using vibro sifter, mix with step (g) granules and transferred into the blender.
j. Sifted Mannitol and Sodium Starch Glycolate through mesh #40 ASTM using vibro sifter and add to step (i) blender containing granules and mix for 10 min at 16 rpm.
k. Sifted Magnesium Stearate through mesh #60 ASTM using vibro sifter and add to step (j) blender containing granules and mix for 3 min at 16 RPM.
l. Compressed the lubricated blend of step (k) with respective punches.
m. Coated the compressed tablet with respective coating material as per unit formula table to achieve the approximate weight gain 3.0% w/w.

Example 3: Process to Prepare the Tablet Composition a. Shifting and Mixing: Co-Sifted MCC, Mannitol, HPC, SSG and Vortioxetine Hydrobromide having PSD of D98 100-200µ, D50 35-90µ and D5 7-30µ through #40 sieve and mixed in RMG, to obtain pre-granulation blend.
b. Granulation: Granulated the pre-granulation blend obtained in step (a) with Purified Water to obtain granules.
c. Drying and Sizing: Dried the granules obtained in step (b), in Fluid Bed dryer to obtain the required LOD and sized through #30 sieve to prepare sized granules.
d. Blending: Blended the sized granules obtained in step (c), with Mannitol and SSG at 16 RPM to obtain pre-lubrication blend.
e. Lubrication: Lubricated with pre-lubrication blend prepared in step (d), with Magnesium Stearate at 16 RPM to obtain lubricated granules.
f. Compression: Compressed the lubricated granules obtained in step (e) into Tablets by using 8.4×5 mm almond shape punch.
g. Coating: Coated the compressed tablet prepared in Step (f), using Opadry suspension to achieve required weight gain.

Example 4: Comparison of In-Vitro Dissolution Profile of Vortioxetine Hydrobromide Tablets 5 mg, 10 mg and 20 mg

| Method | Time points (minutes) | Trintellix ® (Vortioxetine) tablets 5 mg | Vortioxetine tablets 5 mg | Trintellix ® (Vortioxetine) tablets 10 mg | Vortioxetine tablets 10 mg | Trintellix ® (Vortioxetine) tablets 20 mg | Vortioxetine tablets 20 mg |
| --- | --- | --- | --- | --- | --- | --- | --- |
| Paddle, | 5 | 89 | 89 | 85 | 83 | 77 | 82 |
| 50 rpm, | 10 | 96 | 97 | 93 | 99 | 94 | 97 |
| 900 ml, | 15 | 97 | 98 | 95 | 101 | 99 | 100 |
| 0.1N HCl | 30 | 98 | 97 | 96 | 101 | 102 | 101 |
| | 45 | 98 | 97 | 97 | 101 | 102 | 100 |
| F2 value | | 93.61 | | 65.32 | | 76.14 | |

Example 5: In-Vivo Comparison of Vortioxetine Hydrobromide 20 mg Tablets Prepared as Per the Invention, with Trintellix 20 mg Vortioxetine Hydrobromide tablets comprising Vortioxetine Hydrobromide of particle size distribution D98 100-200µ, D50 35-90µ and D5 7-30µ were prepared and were subjected to bioequivalence studies using Trintellix 20 mg as reference composition. The findings are summarized in tables below:

Bioequivalence Summary Table of Cmax:

| Treatment | Ratio | 90% CI |
| --- | --- | --- |
| Test product 20 mg Innovator Product | 94.62 | (86.89, 103.04) |

Bioequivalence Summary Table of AUC0-72

| Treatment | Ratio | 90% CI |
| --- | --- | --- |
| Test product 20 mg Innovator Product | 96.88 | (88.12, 106.51) |

Example 6: Stability Data of Vortioxetine Tablets 5 mg, 10 mg and 20 mg

Figure 1:
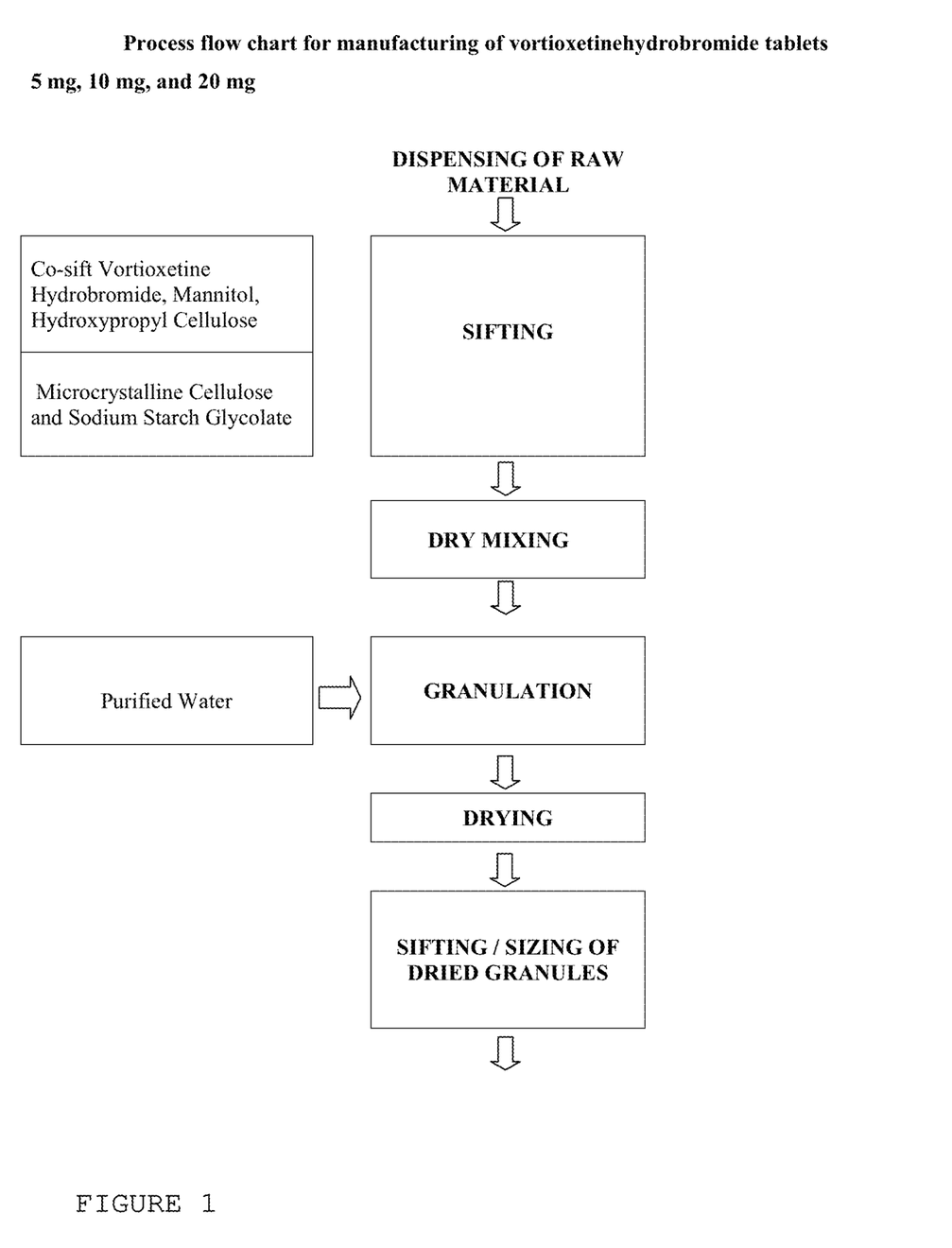
FIG. 1: Process flow chart for manufacturing of vortioxetine hydrobromide tablets 5 mg, 10 mg, and 20 mg
Figure 2:
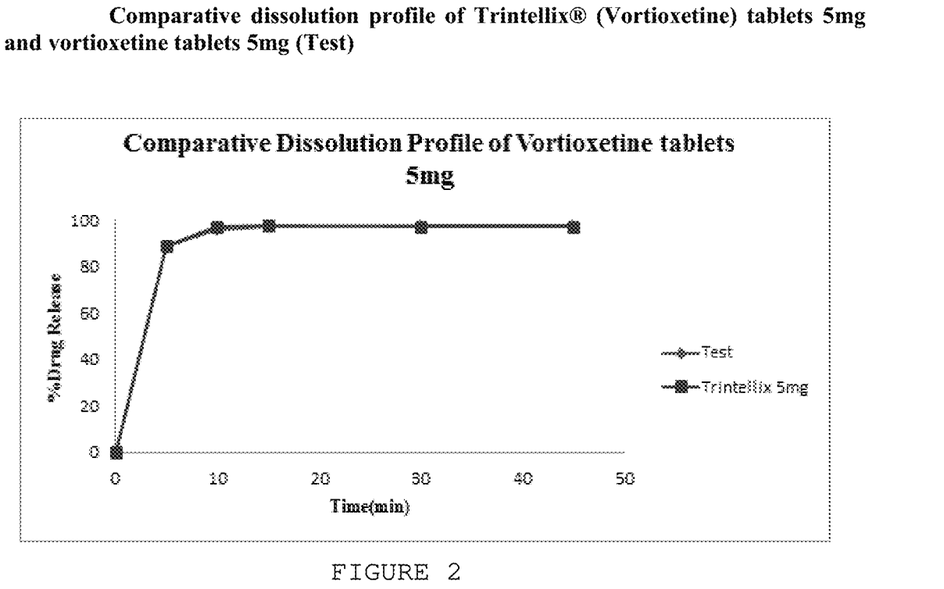
FIG. 2: Comparative dissolution profile of Trintellix® (Vortioxetine) tablets 5 mg and vortioxetine tablets 5 mg (Test)
Figure 3:
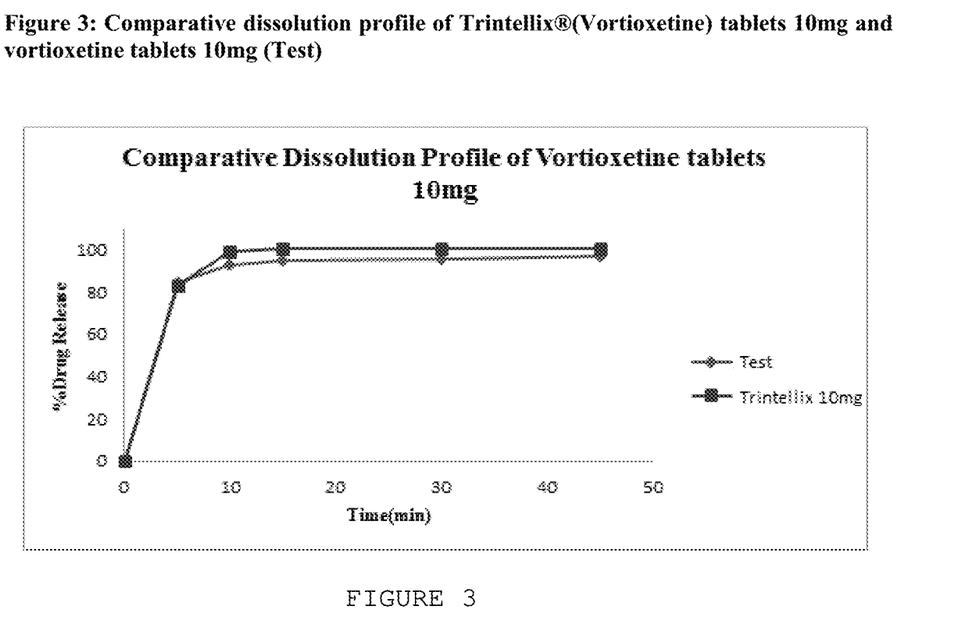
FIG. 3: Comparative dissolution profile of Trintellix® (Vortioxetine) tablets 10 mg and vortioxetine tablets 10 mg (Test)
Figure 4:
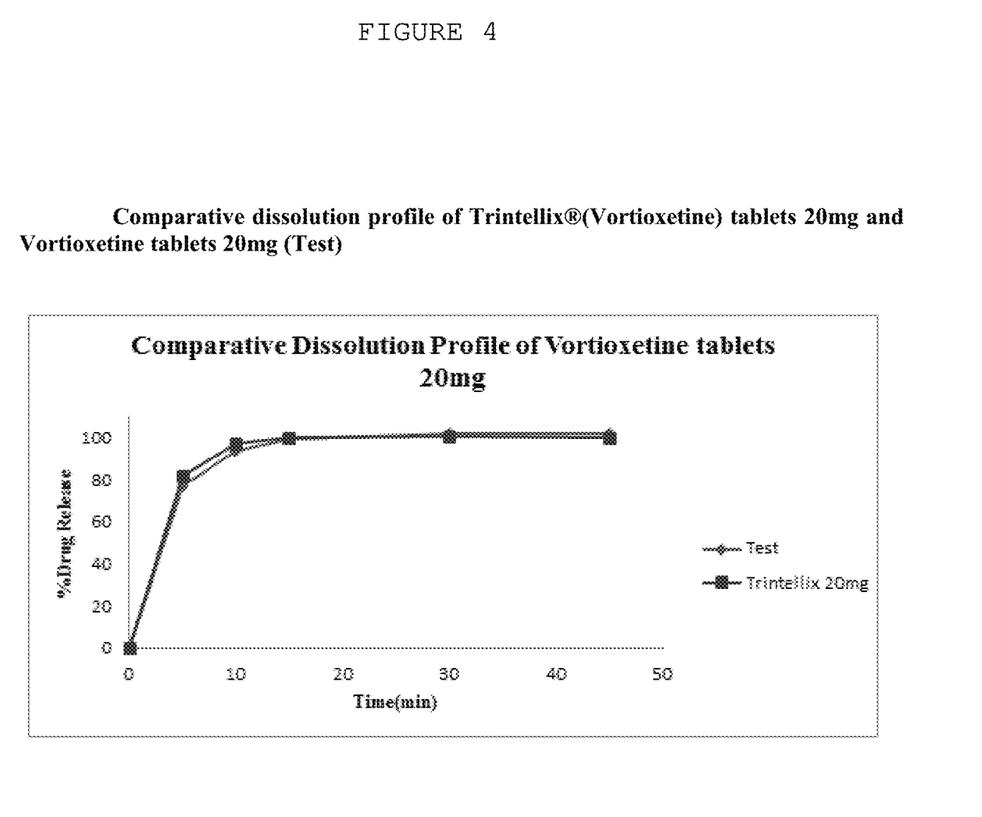
FIG. 4: Comparative dissolution profile of Trintellix® (Vortioxetine) tablets 20 mg and vortioxetine tablets 20 mg (Test)
Figure 5:
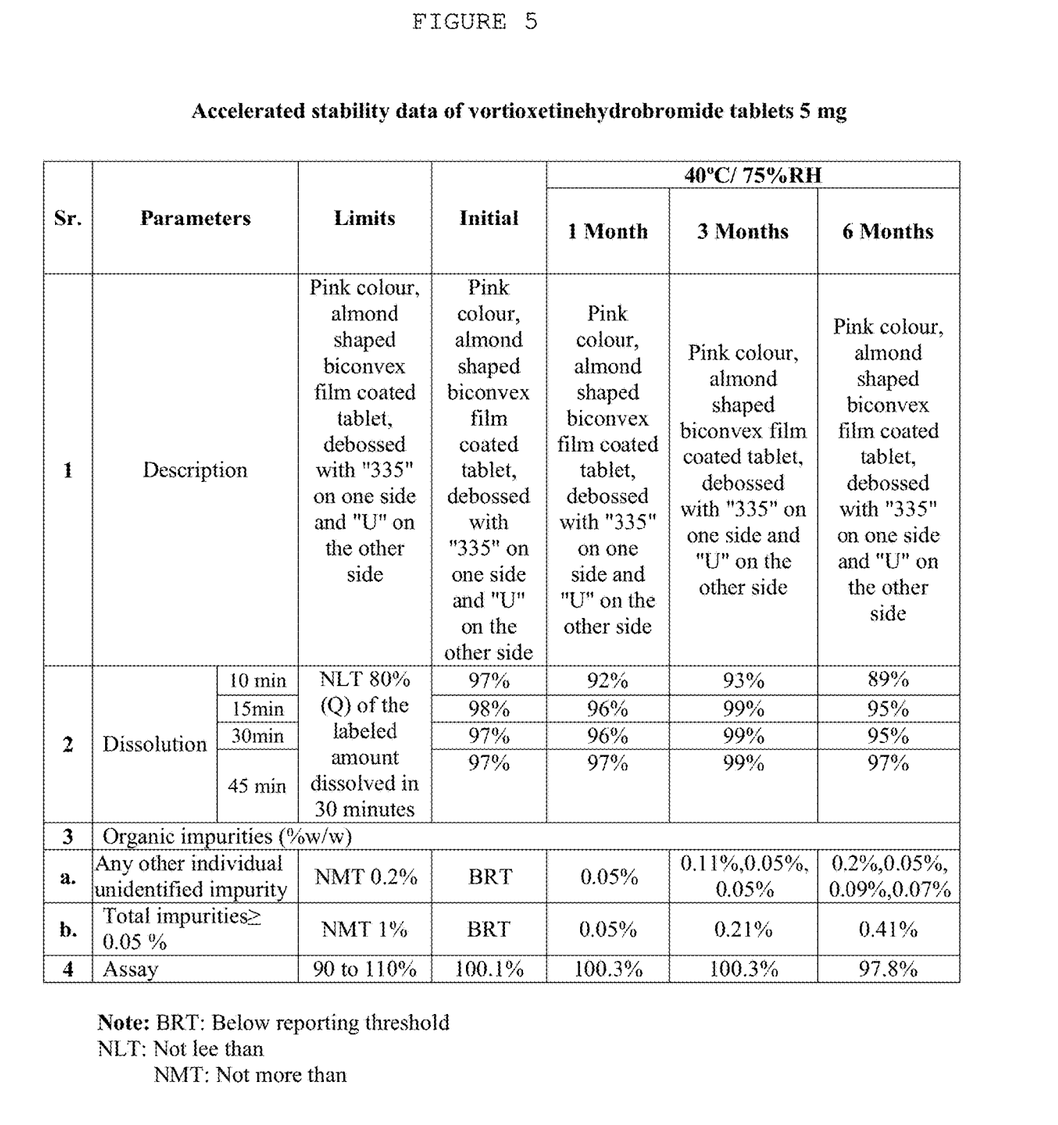
FIG. 5: Accelerated stability data of vortioxetine hydrobromide tablets 5 mg
Figure 6:
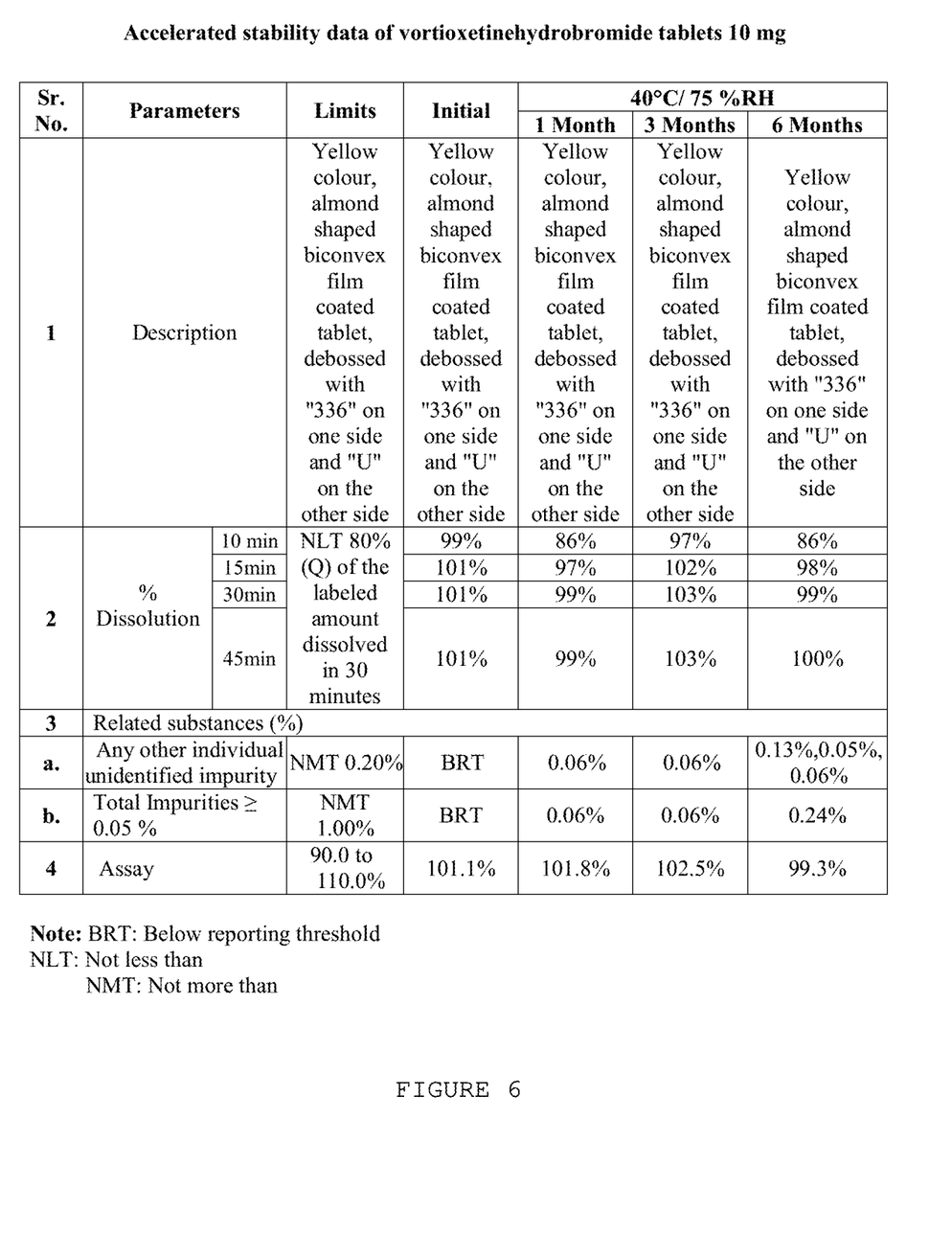
FIG. 6: Accelerated stability data of vortioxetine hydrobromide tablets 10 mg
Figure 7:
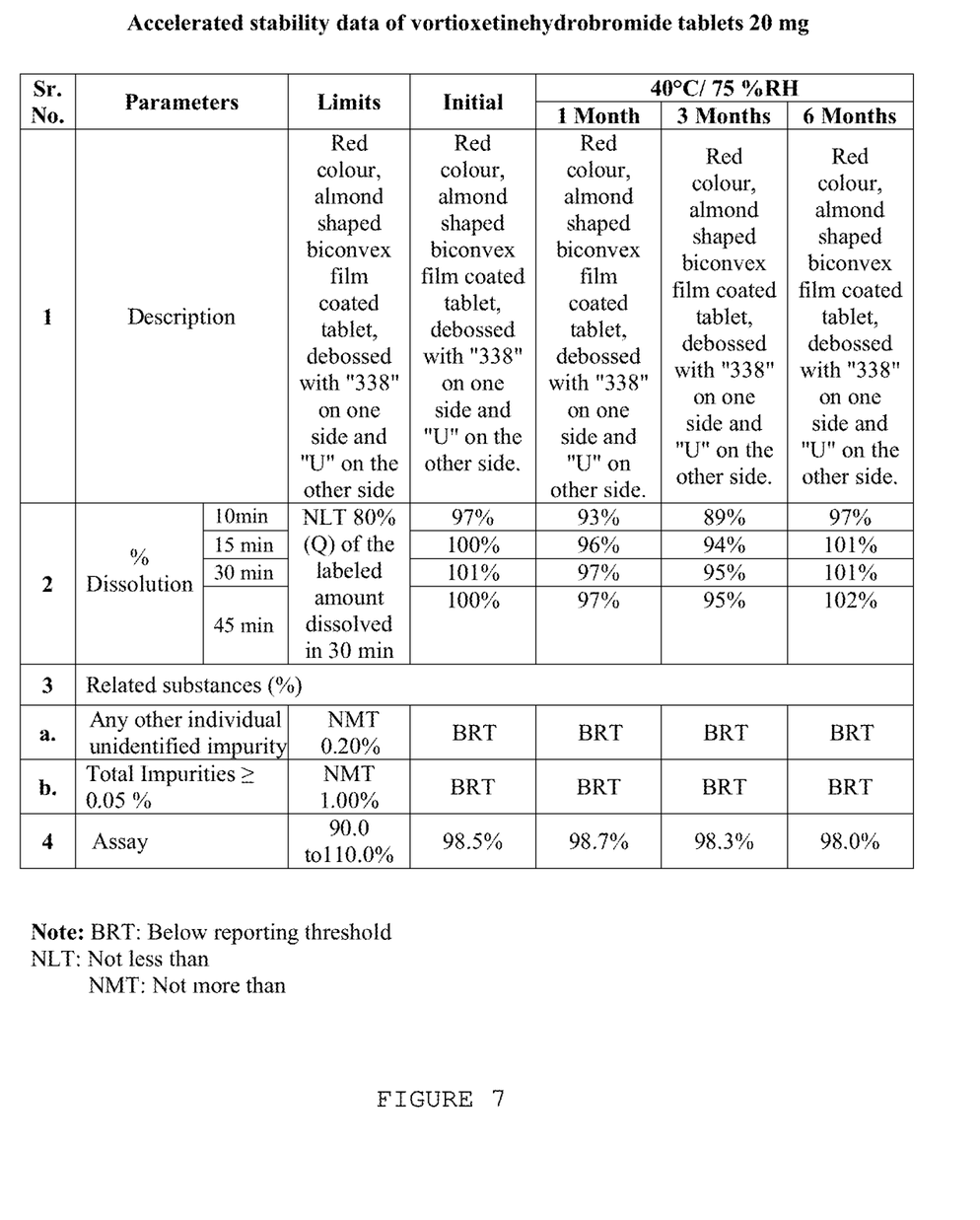
FIG. 7: Accelerated stability data of vortioxetine hydrobromide tablets 20 mg

The stability data of vortioxetine tablets 5 mg, 10 mg and 20 mg obtained as per stability study performed at 40° C./75% RH are shown in FIG. 5, FIG. 6 and FIG. 7 respectively.

We claim:

1. A vortioxetine hydrobromide having particle size distribution corresponding to D98 100-200µ, D50 35-90µ and D5 7-30µ.

2. A pharmaceutical composition comprising vortioxetine hydrobromide having particle size distribution of D98 100-200µ, D50 35-90µ and D5 7-30µ and one or more pharmaceutically acceptable excipients.

3. A process to prepare a pharmaceutical composition comprising the steps of:
   co-sifting vortioxetine hydrobromide having particle size distribution of D98 100-200µ, D50 35-90µ and D5 7-30µ with at least one more ingredient selected from diluent or binder or disintegrant and mixing them to obtain pre-granulation blend;
   granulating the pre-granulation blend obtained in step a. with purified water to obtain granules;
   drying the granules obtained in step b. in fluid bed dryer and sizing through suitable sieve to prepare sized granules;
   blending the sized granules obtained in step c. with other ingredients to obtain pre-lubrication blend;
   lubricating the pre-lubrication blend prepared in step d. to obtain lubricated granules;
   compressing the lubricated granules obtained in step e. into tablets; and
   optionally coating the compressed tablets.

4. The composition according to claim 2, wherein the one or more pharmaceutically acceptable excipients are selected from binders, diluents, disintegrants, lubricants, glidants, coating agents, plasticizers, coloring agent, viscosity enhancers, and the like.

5. The composition according to claim 4 wherein diluent is selected from microcrystalline cellulose, microfine cellulose, mannitol, powdered cellulose, lactose, dibasic calcium phosphate, tribasic calcium phosphate, starch, pre-gelatinized starch, calcium carbonate, calcium sulfate, magnesium carbonate, magnesium oxide, dextrates, dextrin, dextrose, kaolin, maltodextrin, mannitol, sucrose, methyl dextrin and sorbitol and the combinations thereof.

6. The composition according to claim 4 wherein the binder is selected from polyvinylpyrrolidone (povidone, PVP), polyethylene glycol (PEG), cross-linked polyvinylpyrrolidone, cellulose derivatives (such as hydroxymethyl cellulose, hydroxypropylcellulose, carboxy-methylcellulose sodium, ethyl cellulose, hydroxylethylcellulose, hydroxypropylmethylcellulose), sucrose, alginic acid or sodium alginate, carbomer, cottonseed oil, dextrin, dextrose, guar gum, hydrogenated vegetable oil type I, magnesium aluminium silicate, maltodextrin, maltose, polydextrose, polyethylene oxide, stearic acid and zein and the combinations thereof.

7. The composition according to claim 4 wherein the disintegrant is selected form carboxymethylcellulose calcium, carboxymethylcellulose sodium, croscarmellose sodium, crospovidone, polacrilin potassium, sodium alginate and sodium starch glycolate and the combinations thereof.

8. The composition according to claim 4 wherein the lubricant is selected from magnesium stearate, aluminium stearate, sucrose stearate, stearic acid, talc, fumaric acid, palmitic acid, sodium stearyl fumarate, glyceryl monostearate, carnauba wax, hydrogenated vegetable oils, mineral oil, polyethylene glycols and the like and the combinations thereof.

9. The composition according to claim 2, said composition being a tablet and comprising microcrystalline cellulose, mannitol, hydroxypropyl cellulose, sodium starch glycolate and magnesium stearate optionally coated.

10. The composition according to claim 9, said composition being a tablet prepared by wet granulation.

* * * * *